US012576222B2

(12) United States Patent
Waller et al.

(10) Patent No.: US 12,576,222 B2
(45) Date of Patent: Mar. 17, 2026

(54) INHALER WITH BOUNDARY ELEMENT

(71) Applicant: PHILIP MORRIS PRODUCTS S.A., Neuchâtel (CH)

(72) Inventors: Judith Waller, Ostersund (SE); Masja Bertien Mooij, Rotterdam (NL)

(73) Assignee: Philip Morris Products S.A., Neuchâtel (CH)

( * ) Notice: Subject to any disclaimer, the term of this patent is extended or adjusted under 35 U.S.C. 154(b) by 621 days.

(21) Appl. No.: 16/758,110

(22) PCT Filed: Oct. 22, 2018

(86) PCT No.: PCT/IB2018/058208
§ 371 (c)(1),
(2) Date: Apr. 22, 2020

(87) PCT Pub. No.: WO2019/082056
PCT Pub. Date: May 2, 2019

(65) Prior Publication Data
US 2020/0275709 A1 Sep. 3, 2020

(30) Foreign Application Priority Data

Oct. 25, 2017 (EP) .................................... 17198367

(51) Int. Cl.
 *A24F 42/20* (2020.01)
 *A24B 15/16* (2020.01)
 (Continued)

(52) U.S. Cl.
 CPC ........... *A61M 15/003* (2014.02); *A24B 15/16* (2013.01); *A24F 42/20* (2020.01); *A24F 42/60* (2020.01)

(58) Field of Classification Search
 CPC ................................. A24F 42/20; A24F 42/60
 (Continued)

(56) References Cited

U.S. PATENT DOCUMENTS 4,069,819 A * 1/1978 Valentini ........... A61M 15/0033
604/131
6,257,231 B1 7/2001 Shick et al.
(Continued)

FOREIGN PATENT DOCUMENTS

EP 0079478 A1 5/1983
EP 0388621 B1 8/1992
(Continued)

OTHER PUBLICATIONS

International Search Report and Written Opinion issued by the European Patent Office for PCT/IB2018/058208; Feb. 4, 2019; 15 pgs.

(Continued)

*Primary Examiner* — Russell E Sparks
(74) *Attorney, Agent, or Firm* — Mueting Raasch Group

(57) ABSTRACT

An inhaler article (100) includes a body (110) extending along a longitudinal axis ($L_A$) from a mouthpiece end (112) to a distal end (114). A capsule cavity (116) is defined within the body and extends along the longitudinal axis. A mouthpiece air channel (111) extends from the capsule cavity to the mouthpiece end. A boundary element (140) is located between the capsule cavity and the mouthpiece air channel. The boundary element includes at least two concentric rings of apertures (142, 144) fluidly connecting the capsule cavity with the mouthpiece air channel, wherein each of the inner apertures of the inner concentric ring has an open area less than each of the outer apertures of the outer concentric ring of apertures.

20 Claims, 1 Drawing Sheet

(51) Int. Cl.
    *A24F 42/60*     (2020.01)
    *A61M 15/00*     (2006.01)
(58) Field of Classification Search
    USPC .......................................................... 131/329
    See application file for complete search history.

(56) References Cited

U.S. PATENT DOCUMENTS

| | | | |
|---|---|---|---|
| 6,814,786 | B1 | 11/2004 | Zhuang et al. |
| 9,010,323 | B2 | 4/2015 | Haerder et al. |
| 2008/0251072 | A1 | 10/2008 | Lulla et al. |
| 2009/0260623 | A1 | 10/2009 | Dunkley et al. |
| 2016/0354563 | A1 | 12/2016 | Pfrang et al. |
| 2017/0071248 | A1* | 3/2017 | Stenzler ............... A61K 9/0075 |
| 2018/0140789 | A1 | 5/2018 | Pieters et al. |

FOREIGN PATENT DOCUMENTS

| | | | |
|---|---|---|---|
| GB | 1396258 | 6/1975 | |
| RU | 2563795 | 9/2015 | |
| WO | WO 98/26828 A2 | 6/1998 | |
| WO | WO 2002/083220 A2 | 10/2002 | |
| WO | WO 03/051439 A1 | 6/2003 | |
| WO | 20120076479 | 6/2012 | |
| WO | WO 2012/155058 A1 | 11/2012 | |
| WO | WO 2013/008038 A2 | 1/2013 | |
| WO | WO-2015166350 A2 * | 11/2015 | ............ A24B 15/16 |
| WO | WO 2017/079397 A1 | 5/2017 | |
| WO | 20170109678 | 6/2017 | |
| WO | WO 2018/036836 A2 | 3/2018 | |

OTHER PUBLICATIONS

Extended EP Search Report issued by the European Patent Office for EP 17198367.9, Apr. 19, 2018; 9 pgs.

Cohen et al., "GRAS Flavoring Substances," 27. *GRAS Flavoring Substances. Food Technology for Flavoring Extract Manufacturers Association*, Aug. 2015:69(8):40-59.

Hall, R.L. & Oser, B.L., "Recent Progress in the Consideration of Flavoring Ingredients under the Food Additive Amendments 3. GRAS substances," *Food Technology*, Feb. 1965: p. 151-197.

Russian Office Action for RU Application No. 2020116775, issued by the Patent Office of the Russian Federation, Jan. 28, 2022; 16 pgs. including English Translation.

Japanese Office Action for JP 2020-520146 issued by the Japanese Patent Office on Dec. 5, 2022; 10 pgs. including English translation.

Chinese Office Action for CN 201880064237.2 issued by the Chinese Patent Office on Nov. 30, 2022; 18 pgs. including English translation.

\* cited by examiner

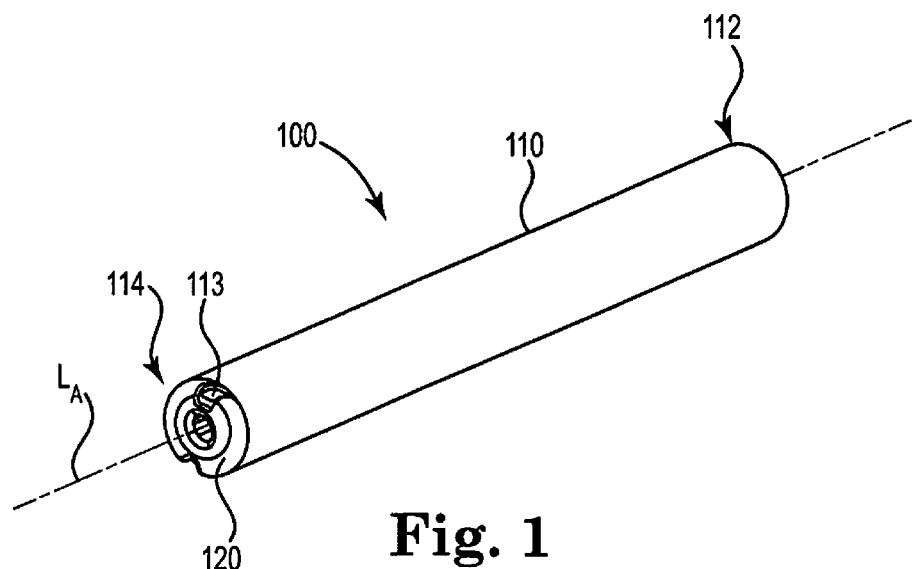
Fig. 1
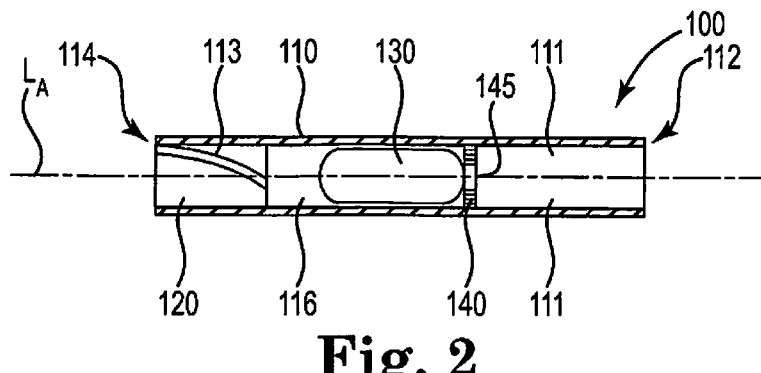
Fig. 2
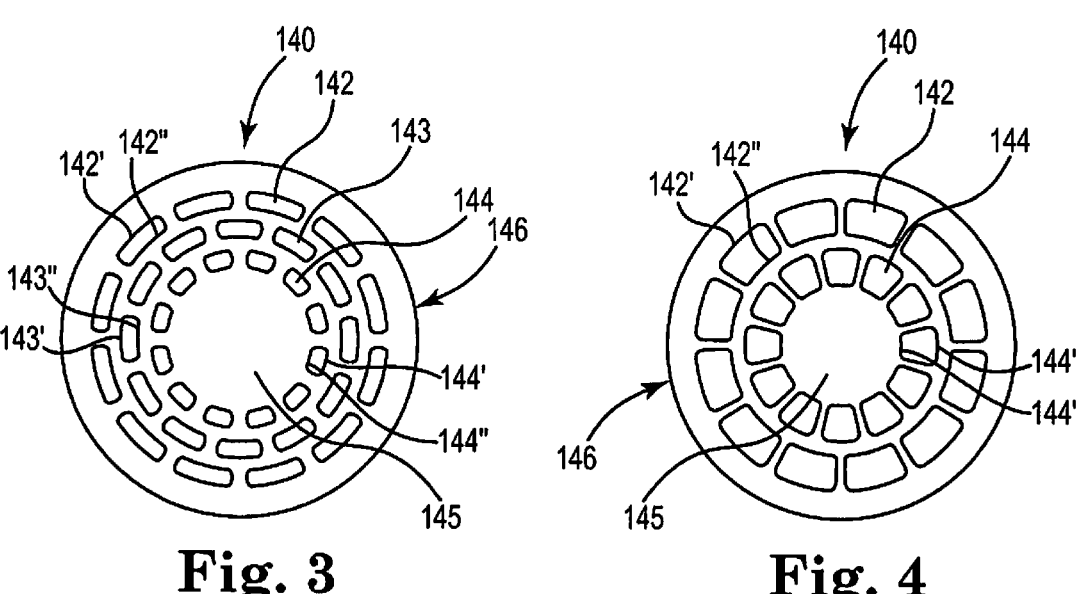
Fig. 3                  Fig. 4

INHALER WITH BOUNDARY ELEMENT

This application is the § 371 U.S. National Stage of International Application No. PCT/IB2018/058208, filed 22 Oct. 2018, which claims the benefit of European Application No. 17198367.9, filed 25 Oct. 2017.

This disclosure relates to an inhaler article that includes a boundary element that fluidly connects a capsule cavity with a mouthpiece channel.

Dry powder inhalers are not always fully suitable to provide dry powder particles to the lungs at inhalation or air flow rates that are within conventional smoking regime inhalation or air flow rates. Dry powder inhalers may be complex to operate or may involve moving parts. Dry powder inhalers often strive to provide an entire dry powder dose or capsule load in a single breath.

It would be desirable to provide a powder inhaler that provides particles to the lungs at inhalation or air flow rates that are within conventional smoking regime inhalation or air flow rates. In particular, it would be desirable to provide a nicotine powder inhaler that provides nicotine particles to the lungs at inhalation or air flow rates that are within conventional smoking regime inhalation or air flow rates. It would be desirable to provide a boundary element within the inhaler article that is configured to provide enhanced airflow or fluid dynamics to maintain stable rotation of a capsule contained within the inhaler article and enhance particle delivery during inhalation. It would also be desirable to provide an inhaler article to deliver nicotine powder with a form similar to a conventional cigarette. It would also be desirable to provide an inhaler article that is simple to manufacture and convenient to use by a consumer.

This disclosure is directed to an inhaler article that includes a body extending along a longitudinal axis from a mouthpiece end to a distal end. A capsule cavity is defined within the body and extends along the longitudinal axis. A mouthpiece air channel extends from the capsule cavity to the mouthpiece end. A boundary element is between the capsule cavity and the mouthpiece air channel. The boundary element includes at least two concentric rings of apertures fluidly connecting the capsule cavity with the mouthpiece air channel.

The boundary element may include a center region having no apertures. In other words, the boundary element may have a center region that is solid. The center region may be any suitable shape. Preferably, the center region is circular. The boundary element may include a solid circular center region. The center region may be co-planar with the remaining portions of the boundary element. The boundary element may define a disc.

The boundary element may comprise a substantially planar upstream surface. The boundary element may comprise a substantially planar downstream surface. The boundary element may be substantially planar. The upstream surface may be a mirror image of the downstream surface. The boundary element may form a substantially planar disc.

The boundary element may extend substantially perpendicular to the longitudinal axis.

The boundary element may define a cross-sectional area. Where the boundary element forms a substantially planar disc, the cross-sectional area of the boundary element may be substantially circular. Where the boundary element extends substantially perpendicular to the longitudinal axis, the cross-sectional area may be a transverse cross-sectional area, relative to the longitudinal axis.

The apertures of the boundary element may be any suitable size and shape. In some embodiments, each aperture may have the same shape. In other embodiments, the apertures may have different sizes and shapes. For example, the apertures of the boundary element may be circular, rectangular or elliptical. Preferably, the apertures are substantially arcuate.

Each aperture of the boundary element may define an open area. The sum of the open areas of the apertures of the boundary element may define a total open area. The proportion of the boundary element surface area that comprises open area may be between about 10% to about 80%, may be between about 20% and about 75%, may be between about 35% and about 70%, may be between about 45% and about 75%, may be between about 50% and about 70% or may be about 60%.

The boundary element may include an outer concentric ring of apertures surrounding an inner concentric ring of apertures. The apertures of the inner concentric ring of apertures may have different sizes and shapes. However, preferably each aperture of the inner concentric ring of apertures has the same size and shape. Similarly, the apertures of the outer concentric ring of apertures may have different sizes and shapes. However, preferably each aperture of the outer concentric ring of apertures has the same size and shape. Each aperture of the inner and outer concentric ring of apertures may define the same open area. However, preferably the apertures of the inner concentric ring of apertures may define a smaller open area than the apertures of the outer concentric ring of apertures. The inner concentric ring of apertures may define a total open area that is less than the total open area of the outer concentric ring of apertures. Preferably the outer concentric ring of apertures surrounds an inner concentric ring of apertures and each of the inner apertures of the inner concentric ring has an open area less than each of the outer apertures of the outer concentric ring of apertures.

The boundary element may have any suitable number of apertures. For example, the boundary element may have between two and fifty apertures. Where the boundary element comprises inner and outer concentric rings of apertures. The outer concentric ring of apertures may contain an equal number of apertures as contained within the inner concentric ring of apertures.

The boundary element may comprise any suitable number of concentric rings of apertures. For example, the boundary element may comprise two, three, four or five concentric rings of apertures. The boundary element may comprise at least two concentric rings of apertures.

This disclosure is directed to a system that includes the inhaler article described herein and a capsule disposed within the capsule cavity. The capsule contains particles including nicotine and optionally a second population of particles that contain flavor that may be larger than the particles including nicotine.

Advantageously, the inhaler article provides nicotine particles to the lungs at inhalation or air flow rates that are within conventional smoking regime inhalation or air flow rates. The inhaler delivers the nicotine powder with an inhaler article that has a form similar to a conventional cigarette. The inhaler article and boundary element may be formed with a simple manufacturing method.

Advantageously, the boundary element concentric ring aperture configuration may provide enhanced airflow or fluid dynamics that may maintain a stable rotation of a capsule contained within the capsule cavity of the inhaler article and enhance particle delivery during inhalation. Advantageously, the boundary element solid (aperture free) planar center region provides enhanced fluid dynamics that may maintain a stable rotation of a capsule contained within the capsule cavity of the inhaler article particle delivery during inhalation.

Advantageously, the boundary element having substantially planar or co-planar upstream and downstream surfaces and without a longitudinal projection, may reduce unwanted recirculation of airflow within the capsule cavity of the inhaler article.

Advantageously, the boundary element concentric ring aperture configuration may facilitate deagglomeration of the particles released from the capsule into the cavity before the particles enter the mouthpiece air channel. Advantageously, the concentric ring aperture configuration may provide increased airflow along the periphery of the boundary element that may reduce airflow turbulence along the capsule.

The inhaler article described herein may provide a dry powder to the lungs at inhalation or air flow rates that are within conventional smoking regime inhalation or air flow rates. A consumer may take a plurality of inhalations or "puffs" where each "puff" delivers a fractional amount of dry powder contained within a capsule contained within the capsule cavity. This inhaler may have a form similar to a conventional cigarette and may mimic the ritual of conventional smoking. This inhaler may be simple to manufacture and convenient to use by a consumer.

Air flow management through the capsule cavity may cause the capsule to rotate during inhalation and consumption. The capsule may contain particles containing nicotine (also referred to as "nicotine powder" or "nicotine particles") and optionally particles comprising flavour (also referred to as "flavour particles"). Rotation of the pierced capsule may suspend and aerosolize the nicotine particles released from the pierced capsule into the inhalation air moving through the inhaler article. The flavour particles may be larger than the nicotine particles and may assist in transporting the nicotine particles into the lungs of the user while the flavour particles preferentially remain in the mouth or buccal cavity of the user. The nicotine particles and optional flavor particles may be delivered with the inhaler article at inhalation or air flow rates that are within conventional smoking regime inhalation or air flow rates.

The term "nicotine" refers to nicotine and nicotine derivatives such as free-base nicotine, nicotine salts and the like.

The term "flavourant" or "flavour" refers to organoleptic compounds, compositions, or materials that alter and are intended to alter the taste or aroma characteristics of nicotine during consumption or inhalation thereof. The term "flavourant" or "flavour" preferably refers to compounds disclosed in the Flavor & Extract Manufacturers Association (FEMA) Flavor Ingredient Library and in particular in the GRAS Flavoring Substances publications 3 to 27, for example, see Hall, R. L. & Oser, B. L., Food Technology, February 1965 pg. 151-197, and in the GRAS flavoring substances 27 S. M. Cohen et al., Food Technology August 2015 pg. 40-59, and intervening GRAS Flavoring Substances publications 4 to 26. For the purpose of this disclosure, nicotine is not considered as a flavourant or flavour.

The inhaler article described herein may be combined with a piercing element or piercing device to deliver the nicotine particles to a consumer. The piercing element or piercing device may be separated from or not form a portion of the inhaler article. A plurality of these inhaler articles may be combined with a piercing element or piercing device to form a kit.

An inhaler article includes a body extending along a longitudinal axis from a mouthpiece end to a distal end. A capsule cavity is defined within the body and extends along the longitudinal axis. A mouthpiece air channel extends from the capsule cavity to the mouthpiece end. A boundary element is between the capsule cavity and the mouthpiece air channel. The boundary element includes at least two concentric rings of apertures fluidly connecting the capsule cavity with the mouthpiece air channel.

The distal end of the inhaler article may include an end cap or endpiece element. An air channel may extend through the end cap or endpiece element to provide airflow through the inhaler article.

The inhaler body may resemble a smoking article or cigarette in size and shape. The inhaler body may have an elongated cylindrical body extending along the longitudinal axis of the inhaler article. The inhaler body may have a substantially uniform outer diameter along the length of the elongated cylindrical body. The inhaler body may have a circular cross-section that may be uniform along the length of the elongated cylindrical body. The inhaler body may have an outer diameter in a range from about 6 mm to about 10 mm, or from about 7 mm to about 10 mm, or about 7 mm to about 9 mm, or about 7 mm to about 8 mm or about 8 mm. The inhaler body may have a length (along the longitudinal axis) in a range from about 40 mm to about 90 mm, or from about 50 mm to about 80 mm, or about 50 mm to about 70 mm, or 55 mm.

The air channel supplying airflow to the capsule cavity may be configured to induce a swirling air flow pattern within the capsule cavity of the inhaler body. The air channel configuration may induce rotational air flow or swirling air flow as the air flows through the air channel and through the capsule cavity. Air flow through the inhaler device may enter the inhaler device at the distal end of the inhaler device and moves along the longitudinal axis of the inhaler device to the mouthpiece end. Air flow through the inhaler device may enter the inhaler device along the inhaler body upstream or along the capsule cavity and move along the longitudinal axis of the inhaler device to the mouthpiece end.

The end cap or endpiece element may include a linear piercing channel extending through the length of the end cap or end piece element. The linear piercing channel may extend along a central axis of the end cap or end piece element. The linear piercing channel may be co-axial with the longitudinal axis of the inhaler body. The linear piercing channel may be sized to allow a piercing element to pass through the linear piercing channel.

The end cap or endpiece element may define a resealable element disposed along or within the linear piercing channel. The resealable element may seal the linear piercing channel. The resealable element may form an airtight seal or barrier along the linear piercing channel, when a piercing element is not within the resealable element. The linear piercing channel may be formed of a pierce-able material. A piercing element may pass through the resealable element and puncture the capsule within the capsule cavity. The resealable element may reseal once the piercing element is retracted or removed from the resealable element. Resealable elements or membranes may include a septum or septum-like element. Resealable elements or membranes may be formed of elastic material such as rubber, silicone, metal foil co-laminated with a polymer, or latex and the like, or cellulose acetate tow, such as high-density cellulose acetate tow.

The capsule cavity may define a cylindrical space configured to contain a capsule (that may have an obround shape, for example). The capsule cavity may have a substantially uniform or uniform diameter along the length of the capsule cavity. The capsule cavity may have a substantially cylindrical or cylindrical cross-section along the length of the capsule cavity. The configuration of the capsule cavity relative to the capsule may promote the capsule to rotate with stability within the capsule cavity. The longitudinal axis of the capsule may rotate with stability co-axially with the longitudinal axis of the inhaler body during inhalation.

Stable rotation refers to the longitudinal axis of the inhaler body being substantially parallel or co-axial with the axis of rotation of the capsule. Stable rotation may refer to the absence of procession of the rotating capsule. Preferably the longitudinal axis of the inhaler body may be substantially coextensive with the axis of rotation of the capsule. Stable rotation of the capsule may provide a uniform entrainment of a portion of nicotine particles from the capsule over two or more, or five or more, or ten or more "puffs" or inhalations by a consumer.

The capsule cavity may have a fixed cavity length. The capsule cavity has a cavity inner diameter, orthogonal to the longitudinal axis, and the capsule has a capsule outer diameter. The capsule cavity may be sized to contain an obround capsule.

The capsule cavity may be bounded on an upstream side by the distal end or end-piece element or end cap and bounded on a downstream side by the boundary element. The end cap or end-piece element and boundary element cooperate to contain the capsule longitudinally within the capsule cavity.

The boundary element described herein provides, at least, surprising provides enhanced fluid or airflow dynamics that may promote stable capsule rotation (during inhalation) and minimize airflow recirculation within the capsule cavity or adjacent to the downstream side of the boundary element.

The boundary element includes at least two concentric rings of apertures fluidly connecting the capsule cavity with the mouthpiece air channel. Each aperture defines a void space or open area that operates as an air duct allowing air and particle-laden air to transmit from the capsule cavity to the mouthpiece air channel.

Each concentric ring of apertures share the same center, or axis, or center axis. The center axis may be coaxial with the longitudinal axis of the inhaler article. The center axis may be coaxial with the axis of rotation of the capsule.

Each concentric ring of apertures may include apertures that define an inner ring perimeter and an outer ring perimeter. Apertures within each concentric ring of apertures are spaced apart from each other with material forming the boundary element, this material connects the inner ring perimeter and an outer ring perimeter to define the total perimeter of each aperture. The apertures may be spaced apart from each other an equal distance within each concentric rings of apertures. The apertures in the outer concentric ring of apertures may be spaced apart further from each other than the inner concentric ring of apertures.

The inner ring perimeter may coincide with a curved inner surface defining an inner surface of each aperture defining the concentric ring of apertures. The outer ring perimeter may coincide with a curved outer surface defining an outer surface of each aperture forming the concentric ring of apertures. The inner ring perimeter and an outer ring perimeter may share the same center, or axis, or center axis. The inner ring perimeter or outer ring perimeter of a concentric ring of apertures (for example, the inner concentric ring of apertures or outer concentric ring of apertures) may preferably coincide with the axis of rotation of the capsule contained within the capsule cavity of the inhaler article.

A diameter segment value measuring a lateral distance between the inner ring perimeter and an outer ring perimeter (of each concentric ring of apertures) may be from about 3% to about 20%, or from about 4% to about 15%, from about 5% to about 11% of the total diameter of the boundary element. Each concentric ring of apertures may have a diameter segment value that are about equal to each other.

The boundary element includes a center region that coincides with the longitudinal axis, and a perimeter region that contacts the body of the inhaler article. The center region may be co-planar with the perimeter region. The boundary element may be substantially planar. The boundary element upstream surface may be free of projections or recesses. The boundary element downstream surface may be free of projections or recesses. The boundary element upstream surface and downstream surface may both be planar and parallel with each other. The boundary element upstream surface and downstream surface may be mirror images of each other.

Advantageously, a planar boundary element, free of projections, extends substantially perpendicularly to the longitudinal axis may facilitate stable rotation of the capsule about the longitudinal axis.

The boundary element may define a disc, being a right circular cylinder whose length, width, or thickness is small compared to its diameter. The boundary element may right circular cylinder whose length, width or thickness is less than about 25% of its diameter, or less than 10% of its diameter.

A planar surface at the center region of boundary element may reduce damage to the capsule during the piercing operation since capsule force against the boundary element is applied to a planar surface area as compared to a projection extending toward the capsule and applying a force to a smaller surface area of the capsule. A planar surface at the center region of boundary element may reduce misalignment of the capsule during a capsule piercing operation, since the capsule remains on the planar surface with the application of force and thus does not "slip" off any feature of the boundary element.

A planar surface at the center region of boundary element may reduce airflow eddy currents or airflow recirculation immediately downstream of the capsule. The planar boundary element may ensure that the capsule remains in tight and close relation to the concentric rings of apertures to minimize drag or the coefficient of drag across the capsule and boundary element. This boundary element may also minimize resistance to draw or "RTD" and aid in providing nicotine delivery to the user at inhalation or air flow rates that are within conventional smoking regime inhalation or air flow rates.

The boundary element center region may be a solid circular region. The solid center region is devoid of apertures, or is free of apertures. Apertures do not extend into or extend through the boundary element solid center region. Fluid or airflow, from the capsule cavity to the mouthpiece air channel, does not transmit or flow through the solid circular region. Fluid or airflow, from the capsule cavity to the mouthpiece air channel, cannot transmit or flow through the solid circular region. The solid circular region has an open area of 0%.

The solid center region may have a diameter of at least about 10%, or at least about 15%, or at least about 20%, or at least about 25%, or at least about 30%, of the total diameter of the boundary element. The solid center region may have a diameter in a range from about 10% to about 75%, or about 15% to about 60%, or about 20% to about 50%, or about 20% to 40%, of the total diameter of the boundary element. The solid center region may have a diameter in a range from about of at least about 1 mm or at least about 2 mm, or in a range from about 1 mm to about 3.5 mm, or from about 1.5 mm to about 3 mm, or from about 2 mm to about 3 mm, and the mesh element may have a diameter in a range from about 5 mm to about 9 mm, or about 6 mm to about 7 mm.

A solid center region surrounded by the concentric ring of apertures, or concentric rings of apertures, may improve or enhanced fluid or airflow dynamics that may promote stable capsule rotation (during inhalation) and minimize airflow recirculation within the capsule cavity or adjacent to the downstream side of the boundary element. For example, airflow transmits through the centric ring of apertures, or concentric rings of apertures, that are adjacent to the outer perimeter of the boundary element, that may stabilize the rotating capsule. Airflow may be minimized along the solid center region, enhancing fluid or airflow dynamics along the capsule, and capsule cavity and through the boundary element.

An outer concentric ring of apertures may surround an inner concentric ring of apertures defined within the boundary element. The inner concentric ring of apertures may have an open area that is less than an open area of the outer concentric ring of apertures. The inner concentric ring of apertures may have an open area that is at least about 10% less than, or at least about 20% less than, or at least about 25% less than, an open area of the outer concentric ring of apertures This configuration may enhance fluid or airflow dynamics to promote stable capsule rotation (during inhalation) and minimize airflow recirculation within the capsule cavity or adjacent to the downstream side of the boundary element. For example, a greater amount of airflow passes through the outer concentric ring of apertures than an inner concentric ring of apertures. This configuration may reduce airflow turbulence along the capsule and capsule cavity and through the boundary element. Preferably, each outer aperture has a open area that is greater than the open area of each inner aperture. Preferably, each inner aperture has an open area that is less than the open area of each outer aperture.

The boundary element has a total open area defined by the summation of the area of all the plurality of apertures defined in the boundary element. This total open area may be between about 10% to about 80%, may be between about 20% and about 75%, may be between about 35% and about 70%, may be between about 45% and about 75%, may be between about 50% and about 70% or may be about 60% of the total boundary element surface area.

An outer ring of apertures may have an equal number of apertures as the inner ring of apertures. In other embodiments, the outer ring of apertures has a greater number of apertures as the inner ring of apertures.

The boundary element may define two concentric rings of apertures. The boundary element may define less than three concentric rings of apertures. The boundary element may define three concentric rings of apertures. The boundary element may define at least three concentric rings of apertures.

In one embodiment the boundary element defines two concentric rings of apertures, where each concentric rings of apertures have an equal or the same number of apertures. The inner concentric ring of apertures may have an open area that is at least about 10% less than, or at least about 20% less than, or at least about 25% less than, an open area of the outer concentric ring of apertures. This boundary element defines a disc having upstream and downstream surfaces that are planar and parallel extending. This boundary element has a solid center region surrounded by the two concentric ring of apertures, where the solid center region is free of apertures and defines a circular region having a diameter in a range from about 20% to about 40%, of the total diameter of the boundary element.

In another embodiment, the boundary element defines three concentric rings of apertures, where each concentric rings of apertures have an equal or the same number of apertures. The innermost concentric ring of apertures may have an open area that is at least about 10% less than, or at least about 20% less than, or at least about 25% less than, an open area of the intermediate concentric ring of apertures. The intermediate concentric ring of apertures may have an open area that is at least about 10% less than, or at least about 20% less than, or at least about 25% less than, an open area of the outer concentric ring of apertures. Thus the inner concentric ring of apertures here may have an open area that is at least about 20% less than, or at least about 40% less than, or at least about 50% less than, an open area of the outer concentric ring of apertures. This boundary element defines a disc having upstream and downstream surfaces that are planar and parallel extending. This boundary element has a solid center region surrounded by the two concentric ring of apertures, where the solid center region is free of apertures and defines a circular region having a diameter in a range from about 20% to about 40%, of the total diameter of the boundary element.

The boundary element may concentric rings of apertures where each aperture has the same radial distance open length or diameter distance (as measured from the axis centerpoint of the boundary element). For example, the boundary element may have a total diameter from about 6 mm to about 8 mm, and each aperture has the same radial distance open length or diameter distance in a range from about 0.2 mm to about 1.2 mm, or from 0.3 mm to about 1 mm, or preferably from about 0.5 mm to about 0.9 mm, or preferably about 0.7 mm.

Apertures that have a radial distance open length or diameter distance in a range from about 0.5 mm to about 0.9 mm has been found to provide particle delivery advantages where a limited amount of particles are attracted to or adhere to (such as, for example, electrostatic bonding) the surface of the boundary element. Apertures that have a radial distance open length or diameter less than about 0.5 mm, or less than 0.4 mm, or less than 0.3 mm has been found to attract or adhere more particles to the surface of the boundary element than apertures that have a radial distance open length or diameter greater than about 0.5 mm.

The boundary element having more open area in the outer con concentric ring of apertures than an inner concentric ring of apertures has been shown to provide more airflow per unit area to the outer vs. inner apertures. This has been shown to advantageously improve the airflow characteristics of the inhaler and may reduce air flow turbulence through the inhaler.

The solid portions of the boundary element separating the apparatus within each concentric rings of apertures from each other has a circumferential distance closed length or distance. Preferably the solid portions of the boundary element separating the apparatus within outer concentric ring of apertures from each other has a circumferential distance closed length or distance that is greater than the solid portions of the boundary element separating the apparatus within inner concentric ring of apertures. In other words, solid spaces between adjacent apertures is preferably greater in the outer ring than the inner ring.

The boundary element may be integrally formed with the body of the inhaler article. The boundary element may be formed of the same material as the body of the inhaler article. The boundary element may be formed of a thermoplastic material. The boundary element may be formed of a cellulosic material. The boundary element may be formed of biodegradable material.

The boundary element may be integrally formed with the body of the inhaler article via simultaneous moulding. The boundary element may be integrally formed with the body of the inhaler article via sequential moulding of the either the boundary element or the inhaler body and then moulding the remaining boundary element or the inhaler body. A boundary element integrally moulded with the inhaler body may provide improved assemble and manufacture of the inhaler device. The configuration of the boundary element may also lend itself to these moulding techniques.

The capsule may be sealed within the inhaler article prior to consumption. The inhaler article may be contained within a sealed or airtight container or bag. The inhaler article may include one or more peelable or removable seal layers to cover the one or more air inlet channels or the air outlet or mouthpiece of the inhaler article.

The capsule may rotate about its longitudinal or central axis when air flows through the inhaler article. The capsule may be formed of an airtight material that may be pierced or punctured by a piercing element that may be separate or combined with the inhaler. The capsule may formed of a metallic or polymeric material that serves to keep contaminates out of the capsule but may be pierced or punctured by a piercing element prior to consumption of the nicotine particles within the capsule. The capsule may be formed of a polymer material. The polymer material may be hydroxypropylmethylcellulose (HPMC). The capsule may be a size 1 to size 4 capsule, or a size 3 capsule.

A separate piercing element, such as a metal or rigid needle, may form a single aperture through the capsule received in the capsule cavity. The piercing element may pass through the resealable element sealing the piercing channel on the end cap.

The capsule contains nicotine particles comprising nicotine (also referred to as "nicotine powder" or "nicotine particles") and optionally particles comprising flavour (also referred to as "flavour particles). The capsule may contain a predetermined amount of nicotine particles and optional flavour particles. The capsule may contain enough nicotine particles to provide at least 2 inhalations or "puffs", or at least about 5 inhalations or "puffs", or at least about 10 inhalations or "puffs". The capsule may contain enough nicotine particles to provide from about 5 to about 50 inhalations or "puffs", or from about 10 to about 30 inhalations or "puffs". Each inhalation or "puff" may deliver from about 0.1 mg to about 3 mg of nicotine particles to the lungs of the user or from about 0.2 mg to about 2 mg of nicotine particles to the lungs of the user or about 1 mg of nicotine particles to the lungs of the user.

The nicotine particles may have any useful concentration of nicotine based on the particular formulation employed. The nicotine particles may have at least about 1% wt nicotine up to about 30% wt nicotine, or from about 2% wt to about 25% wt nicotine, or from about 3% wt to about 20% wt nicotine, or from about 4% wt to about 15% wt nicotine, or from about 5% wt to about 13% wt nicotine. Preferably, about 50 to about 150 micrograms of nicotine may be delivered to the lungs of the user with each inhalation or "puff".

The capsule may hold or contain at least about 5 mg of nicotine particles or at least about 10 mg of nicotine particles. The capsule may hold or contain less than about 900 mg of nicotine particles, or less than about 300 mg of nicotine particles, or less than 150 mg of nicotine particles. The capsule may hold or contain from about 5 mg to about 300 mg of nicotine particles or from about 10 mg to about 200 mg of nicotine particles.

When flavour particles are blended or combined with the nicotine particles within the capsule, the flavour particles may be present in an amount that provides the desired flavour to each inhalation or "puff" delivered to the user.

The nicotine particles may have any useful size distribution for inhalation delivery preferentially into the lungs of a user. The capsule may include particles other than the nicotine particles. The nicotine particles and the other particles may form a powder system.

The capsule may hold or contain at least about 5 mg of a dry powder (also referred to as a powder system) or at least about 10 mg of a dry powder. The capsule may hold or contain less than about 900 mg of a dry powder, or less than about 300 mg of a dry powder, or less than about 150 mg of a dry powder. The capsule may hold or contain from about 5 mg to about 300 mg of a dry powder, or from about 10 mg to about 200 mg of a dry powder.

The dry powder or powder system may have at least about 40%, or at least about 60%, or at least about 80%, by weight of the powder system comprised in nicotine particles having a particle size of about 5 micrometers or less, or in a range from about 1 micrometer to about 5 micrometres.

The particles comprising nicotine may have a mass median aerodynamic diameter of about 5 micrometres or less, or in a range from about 0.5 micrometres to about 4 micrometres, or in a range from about 1 micrometres to about 3 micrometres or in a range from about 1.5 micrometres to about 2.5 micrometres. The mass median aerodynamic diameter is preferably measured with a cascade impactor.

The particles comprising flavour may have a mass median aerodynamic diameter of about 20 micrometres or greater, or about 50 micrometres or greater, or in a range from about 50 to about 200 micrometres, or from about 50 to about 150 micrometres. The mass median aerodynamic diameter is preferably measured with a cascade impactor.

The dry powder may have a mean diameter of about 60 micrometres or less, or in a range from about 1 micrometres to about 40 micrometres, or in a range from about 1.5 micrometres to about 25 micrometres. The mean diameter refers to the mean diameter per mass and is preferably measured by laser diffraction, laser diffusion or an electronic microscope.

Nicotine in the powder system or nicotine particles may be a pharmaceutically acceptable free-base nicotine, or nicotine salt or nicotine salt hydrate. Useful nicotine salts or nicotine salt hydrates include nicotine pyruvate, nicotine citrate, nicotine aspartate, nicotine lactate, nicotine bitartrate, nicotine salicylate, nicotine fumarate, nicotine monopyruvate, nicotine glutamate or nicotine hydrochloride, for example. The compound combining with nicotine to form the salt or salt hydrate may be chosen based on its expected pharmacological effect.

The nicotine particles preferably include an amino acid. Preferably the amino acid may be leucine such as L-leucine. Providing an amino acid such as L-leucine with the particles comprising nicotine, may reduce adhesion forces of the particles comprising nicotine and may reduce attraction between nicotine particles and thus reduce agglomeration of nicotine particles. Similarly, adhesion forces to particles comprising flavour may also be reduced thus agglomeration of nicotine particles with flavour particles is also reduced. The powder system described herein thus may be a free flowing material and possess a stable relative particle size of each powder component even when the nicotine particles and the flavour particles are combined.

Preferably, the nicotine may be a surface modified nicotine salt where the nicotine salt particle comprises a coated or composite particle. A preferred coating or composite material may be L-leucine. One particularly useful nicotine particle may be nicotine bitartrate with L-leucine.

The powder system may include a population of flavour particles. The flavour particles may have any useful size distribution for inhalation delivery selectively into the mouth or buccal cavity of a user.

The powder system may have at least about 40%, or at least about 60%, or at least about 80%, by weight of the population of flavour particles of the powder system comprised in particles having a particle size of about 20 micrometres or greater. The powder system may have at least about 40% or at least about 60%, or at least about 80%, by weight of the population of flavour particles of the powder system comprised in particles having a particle size of about 50 micrometres or greater. The powder system may have at least about 40% or at least about 60%, or at least about 80%, by weight of the population of flavour particles of the powder system comprised in particles having a particle size in a range from about 50 micrometer to about 150 micrometres.

Flavourants or flavours may be provided as a solid flavour (at room temperature of about 22 degrees centigrade and one atmosphere pressure) and may include flavour formulations, flavour-containing materials and flavour precursors. The flavourant may include one or more natural flavourants, one or more synthetic flavourants, or a combination of natural and synthetic flavourants. Flavourants as described herein are organoleptic compounds, compositions, or materials that are selected and utilized to alter or are intended to alter the taste or aroma characteristics of the nicotine component during consumption or inhalation thereof.

Flavourants or flavours refer to a variety of flavour materials of natural or synthetic origin. They include single compounds and mixtures. The flavour or flavourant has flavour properties that may enhance the experience of the nicotine component during consumption. The flavour may be chosen to provide an experience similar to that resulting from smoking a combustible smoking article. For example, the flavour or flavourant may enhance flavour properties such as mouth fullness and complexity. Complexity is generally known as the overall balance of the flavour being richer without dominating single sensory attributes. Mouth fullness is described as perception of richness and volume in the mouth and throat of the consumer.

Suitable flavours include, but are not limited to, any natural or synthetic flavour, such as tobacco, smoke, menthol, mint (such as peppermint and spearmint), chocolate, licorice, citrus and other fruit flavours, gamma octalactone, vanillin, ethyl vanillin, breath freshener flavours, spice flavours such as cinnamon, methyl salicylate, linalool, bergamot oil, geranium oil, lemon oil, and ginger oil, and the like.

Other suitable flavours may include flavour compounds selected from the group consisting of an acid, an alcohol, an ester, an aldehyde, a ketone, a pyrazine, combinations or blends thereof and the like. Suitable flavour compounds may be selected, for example, from the group consisting of phenylacetic acid, solanone, megastigmatrienone, 2-heptanone, benzylalcohol, cis-3-hexenyl acetate, valeric acid, valeric aldehyde, ester, terpene, sesquiterpene, nootkatone, maltol, damascenone, pyrazine, lactone, anethole, iso-s valeric acid, combinations thereof, and the like.

Further specific examples of flavours may be found in the current literature, and are well-known to the person skilled in the art of flavouring, i.e. of imparting an odor or taste to a product.

The flavourant may be a high potency flavourant, and may be used and detected at levels that would result in less than 200 parts per million in inhalation air flow. Examples of such flavourants are key tobacco aroma compounds such as beta-damascenone, 2-ethyl-3,5-dimethylpyrazine, phenylacetaldehyde, guaiacol, and furaneol. Other flavourants may only be sensed by humans at higher concentration levels. These flavourants, which are referred to herein as the lower potency flavourants, are typically used at levels that results in orders of magnitude higher amounts of flavourant released into the inhalation air. Suitable lower potency flavourants include, but are not limited to, natural or synthetic menthol, peppermint, spearmint, coffee, tea, spices (such as cinnamon, clove and ginger), cocoa, vanilla, fruit flavours, chocolate, eucalyptus, geranium, eugenol and linalool.

The particles comprising flavour may include a compound to reduce adhesion forces or surface energy and resulting agglomeration. The flavour particle may be surface modified with an adhesion reducing compound to form a coated flavour particle. One preferred adhesion reducing compound may be magnesium stearate. Providing an adhesion reducing compound such as magnesium stearate with the flavour particle, especially coating the flavour particle, may reduce adhesion forces of the particles comprising flavour and may reduce attraction between flavour particles and thus reduce agglomeration of flavour particles. Thus agglomeration of flavour particles with nicotine particles may also be reduced. The powder system described herein thus may possess a stable relative particle size of the particles comprising nicotine and the particles comprising flavour even when the nicotine particles and the flavour particles are combined. The powder system preferably may be free flowing.

Conventional formulations for dry powder inhalation contain carrier particles that serve to increase the fluidization of the active particles since the active particles may be too small to be influenced by simple airflow though the inhaler. The powder system may comprise carrier particles. These carrier particles may be a saccharide such as lactose or mannitol that may have a particle size greater than about 50 micrometres. The carrier particles may be utilized to improve dose uniformity by acting as a diluent or bulking agent in a formulation.

The powder system utilized with the nicotine powder delivery system described herein may be carrier-free or substantially free of a saccharide such as lactose or mannitol. Being carrier-free or substantially free of a saccharide such as lactose or mannitol may allow the nicotine and to be inhaled and delivered to the user's lungs at inhalation or airflow rates that are similar to typical smoking regime inhalation or airflow rates.

The nicotine particles and a flavour may be combined in a single capsule. As described above, the nicotine particles and a flavour may each have reduced adhesion forces that result in a stable particle formulation where the particle size of each component does not substantially change when combined. Alternatively, the powder system includes nicotine particles contained within a single capsule and the flavour particles contained within a second capsule.

The nicotine particles and flavour particles may be combined in any useful relative amount so that the flavour particles are detected by the user when consumed with the nicotine particles. Preferably the nicotine particles and a flavour particles form at least about 90% wt or at least about 95% wt or at least about 99% wt or 100% wt of the total weight of the powder system.

The inhaler and inhaler system may be less complex and have a simplified airflow path as compared to conventional dry powder inhalers. Advantageously, rotation of the capsule within the inhaler body aerosolizes the nicotine particles or powder system and may assist in maintaining a free flowing powder. Thus, the inhaler article may not require the elevated inhalation rates typically utilized by conventional inhalers to deliver the nicotine particles described above deep into the lungs.

The inhaler article may use a flow rate of less than about 5 L/min or less than about 3 L/min or less than about 2 L/min or about 1.6 L/min. Preferably, the flow rate may be in a range from about 1 L/min to about 3 L/min or from about 1.5 L/min to about 2.5 L/min. Preferably, the inhalation rate or flow rate may be similar to that of Health Canada smoking regime, that is, about 1.6 L/min.

The inhaler may be used by a consumer like smoking a conventional cigarette or vaping an electronic cigarette. Such smoking or vaping may be characterized by two steps: a first step during which a small volume containing the full amount of nicotine desired by the consumer is drawn into the mouth cavity, followed by a second step during which this small volume comprising the aerosol comprising the desired amount of nicotine is further diluted by fresh air and drawn deeper into the lungs. Both steps are controlled by the consumer. During the first inhalation step the consumer may determine the amount of nicotine to be inhaled. During the second step, the consumer may determine the volume for diluting the first volume to be drawn deeper into the lungs, maximizing the concentration of active agent delivered to the airway epithelial surface. This smoking mechanism is sometimes called "puff-inhale-exhale".

All scientific and technical terms used herein have meanings commonly used in the art unless otherwise specified. The definitions provided herein are to facilitate understanding of certain terms used frequently herein.

The terms "upstream" and "downstream" refer to relative positions of elements of the inhaler described in relation to the direction of inhalation air flow as it is drawn through the body of the inhaler from a distal end portion to the mouthpiece portion.

As used herein, the singular forms "a", "an", and "the" encompass embodiments having plural referents, unless the content clearly dictates otherwise.

As used herein, "or" is generally employed in its sense including "and/or" unless the content clearly dictates otherwise. The term "and/or" means one or all of the listed elements or a combination of any two or more of the listed elements.

As used herein, "have", "having", "include", "including", "comprise", "comprising" or the like are used in their open ended sense, and generally mean "including, but not limited to". It will be understood that "consisting essentially of", "consisting of", and the like are subsumed in "comprising," and the like.

The words "preferred" and "preferably" refer to embodiments of the invention that may afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the disclosure, including the claims.

FIG. 1 is a perspective view of an illustrative inhaler article.

FIG. 2 is a cross-sectional schematic diagram of the illustrative inhaler article of FIG. 1 along the longitudinal axis.

FIG. 3 and FIG. 4 are plan views of illustrative boundary elements according to the present invention.

The schematic drawings are not necessarily to scale and are presented for purposes of illustration and not limitation. The drawings depict one or more aspects described in this disclosure. However, it will be understood that other aspects not depicted in the drawing fall within the scope and spirit of this disclosure.

FIG. 1 and FIG. 2 illustrate an exemplary inhaler article 100. FIG. 2 is a cross-sectional schematic diagram of the illustrative inhaler article of FIG. 1 along the longitudinal axis. The inhaler article 100 includes a body 110 extending along a longitudinal axis $L_A$ from a mouthpiece end 112 to a distal end 114 and a capsule cavity 116 defined within the body 110. The body is a substantially cylindrical tubular body. The body 110 may have a uniform external or outer diameter of about 7.5 mm and a length of about 55 mm. The body 110 may have a uniform inner diameter of about 6.5 mm. The body 110 may have a uniform thickness about 1 mm.

A mouthpiece air channel 111 extends from the capsule cavity 116 to the mouthpiece end 112. An end cap or end element 120 is disposed within the distal end 112 and extends to the capsule cavity 116. The end cap or end element 120 includes an air channel 113 extending along the end cap or end element 120. The air channel 113 is non-parallel with the longitudinal axis $L_A$ to assist in inducing a swirling airflow thought the capsule cavity 116 when air is drawn through the cavity towards the mouthpiece air channel 111. In some embodiments, the end cap 120 may include two or more air channels 113 spaced around the circumference of the end cap 120.

The end cap or end element 120 and a boundary element 140 bound the capsule cavity 116. A capsule 130 is disposed within the cavity 116. The capsule 130 contains particles comprising nicotine. The end cap or end element 120 and the boundary element 140 cooperate to contain the capsule 130 longitudinally within the capsule cavity 116. Drawing air through the end cap 120 towards the mouthpiece air channel 111 may induce swirling airflow in the cavity which may induce rotation of the capsule 130. The capsule 130 axis of rotation may be coextensive with the longitudinal axis $L_A$. The boundary element 140 defies a disc shape having a length or thickness of about 0.5 mm and a diameter of about 6.5 mm or about equal to the inner diameter of the body 110.

FIG. 3 and FIG. 4 are plan views of illustrative boundary elements 140. The boundary element 140 has a center region 145 that coincides with the longitudinal axis $L_A$, and a perimeter region 146 that contacts the body 110 (illustrated in FIG. 2). The center region 145 is illustrated as co-planar with the perimeter region 146. The boundary elements 140 may be a planar body being free of projections extending along the longitudinal axis $L_A$.

FIG. 3 illustrates a boundary element 140 defining three concentric rings of apertures 142, 143, 144. A center concentric rings of apertures 143 is disposed between an inner concentric ring of apertures 144 and an outer concentric ring of apertures 142. The three concentric rings of apertures 142, 143, 144 each contain an equal number of apertures (12 are illustrated). A diameter segment value measuring a lateral distance between the inner ring perimeter 142", 143", 144" and an outer ring perimeter 142', 143', 144' forming each concentric rings of apertures 142, 143, 144 are equal and about 4% to about 5% (0.3 mm) of the total diameter (6.5 mm) of the boundary element 140. The inner concentric ring of apertures 144 has an open area that is less than the open area of either of the outer concentric ring of apertures 142 or the center concentric ring of apertures 143. The center concentric ring of apertures 143 has an open area that is less than the open area of the outer concentric ring of apertures 142 and greater than the open area of the inner concentric ring of apertures 144. The outer concentric ring of apertures 144 has an open area that is greater than the open area of either of the inner concentric ring of apertures 144 or the center concentric ring of apertures 143. Apertures within each concentric ring of apertures are spaced apart from each other with material forming the boundary element. In FIG. 3, the apertures are spaced apart from each other an equal distance within each concentric rings of apertures 142, 143, 144.

FIG. 4 illustrates a boundary element 140 defining two concentric rings of apertures 142, 144. An inner concentric ring of apertures 144 is disposed between the solid center region 145 and an outer concentric ring of apertures 142. The two concentric rings of apertures 142, 144 each contain an equal number of apertures (12 are illustrated). A diameter segment value measuring a lateral distance between the inner ring perimeter 142", 144" and an outer ring perimeter 142', 144' forming each concentric rings of apertures 142, 144 are equal and about 10% to about 11% (0.7 mm) of the total diameter (6.5 mm) of the boundary element 140. The inner concentric ring of apertures 144 has an open area that is less than the open area of the outer concentric ring of apertures 142. In FIG. 4, the apertures in the outer concentric ring of apertures 142 are spaced apart further from each other (a distance of about 0.4 mm) than the inner concentric ring of apertures 144 (a distance of about 0.4 mm).

The invention claimed is:

1. An inhaler article comprising:
a body extending along a longitudinal axis from a mouthpiece end to a distal end;
a capsule cavity defined within the body and extending along the longitudinal axis;
a capsule disposed within the capsule cavity;
a mouthpiece air channel extending from the capsule cavity to the mouthpiece end;
a boundary element between the capsule cavity and the mouthpiece air channel, the boundary element comprising at least two concentric rings of apertures fluidly connecting the capsule cavity with the mouthpiece air channel, a center region that coincides with the longitudinal axis, and a perimeter that contacts the body, and the center region is an aperture-free solid circular region co-planar with the perimeter;
an outer concentric ring of apertures surrounds an inner concentric ring of apertures and each of the inner apertures of the inner concentric ring has an open area less than each of the outer apertures of the outer concentric ring of apertures.

2. The inhaler article according to claim 1, wherein the inner concentric ring of apertures has an open area that is less than an open area of the outer concentric ring of apertures.

3. The inhaler article according to claim 2, wherein the outer ring of apertures has equal number of apertures as the inner ring of apertures.

4. The inhaler article according to claim 1, wherein each concentric ring of apertures has a diameter segment value measuring a lateral distance between an inner ring perimeter and an outer ring perimeter forming each concentric ring of apertures, each diameter segment value are equal and each are about 4% to about 15% of a total diameter of the boundary element.

5. The inhaler article according to claim 1, wherein the boundary element center region has a diameter in a range from about 20% to about 50%, of the total diameter of the boundary element.

6. The inhaler article according to claim 1, wherein the boundary element comprises three concentric rings of apertures.

7. The inhaler article according to claim 1, wherein the boundary element is integrally formed with the body of the inhaler article.

8. The inhaler article according to claim 1, wherein the boundary element is formed of the same material as the body of the inhaler article.

9. The inhaler article according to claim 1, wherein the apertures of the boundary element define a total open area that is in a range from about 45% to about 75% of the total boundary element surface area.

10. The inhaler article according to claim 1, wherein the body has an outer diameter that is substantially constant from the distal end to the mouthpiece end.

11. The inhaler article of claim 1, the capsule containing particles comprising nicotine, the particles having a mass median aerodynamic diameter in a range from about 1 micrometre to about 5 micrometres.

12. The inhaler article of claim 11, wherein the capsule further contains a second population of particles having a mass median aerodynamic diameter in a range from about 50 to about 200 micrometres, and the second population of particles comprise particles comprising flavour.

13. The inhaler article of claim 11, wherein the capsule rotates about an axis of rotation and the axis of rotation is coincident with the center axis of each concentric ring of apertures.

14. The inhaler article according to claim 2, wherein each concentric ring of apertures has a diameter segment value measuring a lateral distance between an inner ring perimeter and an outer ring perimeter forming each concentric ring of apertures, each diameter segment value are equal and each are about 4% to about 15% of a total diameter of the boundary element.

15. The inhaler article according to claim 3, wherein each concentric ring of apertures has a diameter segment value measuring a lateral distance between an inner ring perimeter and an outer ring perimeter forming each concentric ring of apertures, each diameter segment value are equal and each are about 4% to about 15% of a total diameter of the boundary element.

16. The inhaler article according to claim 2, wherein the boundary element center region has a diameter in a range from about 20% to about 50%, of the total diameter of the boundary element.

17. The inhaler article according to claim 3, wherein the boundary element center region has a diameter in a range from about 20% to about 50%, of the total diameter of the boundary element.

18. The inhaler article according to claim 4, wherein the boundary element center region has a diameter in a range from about 20% to about 50%, of the total diameter of the boundary element.

19. The inhaler article according to claim 14, wherein the boundary element center region has a diameter in a range from about 20% to about 50%, of the total diameter of the boundary element.

20. The inhaler article according to claim 15, wherein the boundary element center region has a diameter in a range from about 20% to about 50%, of the total diameter of the boundary element.

\* \* \* \* \*